United States Patent [19]

Kilminster et al.

[11] Patent Number: 4,775,616

[45] Date of Patent: Oct. 4, 1988

[54] CYAN DYE-FORMING COUPLERS AND PHOTOGRAPHIC MATERIALS CONTAINING SAME

[75] Inventors: Kenneth N. Kilminster; David Hoke, both of Rochester, N.Y.

[73] Assignee: Eastman Kodak Company, Rochester, N.Y.

[21] Appl. No.: 940,829

[22] Filed: Dec. 12, 1986

[51] Int. Cl.$^4$ .................................................. G03C 7/34
[52] U.S. Cl. .................................... 430/552; 430/553
[58] Field of Search ................................. 430/552, 553

[56] References Cited

U.S. PATENT DOCUMENTS 4,333,999  6/1982  Lau ................................. 430/552 X
4,609,619  9/1986  Katoh et al. ....................... 430/553

FOREIGN PATENT DOCUMENTS 111643  6/1984  Japan .
111644  6/1984  Japan .
105644  6/1984  Japan .

Primary Examiner—Paul R. Michl
Assistant Examiner—Lee C. Wright
Attorney, Agent, or Firm—Thomas F. Kirchoff

[57] ABSTRACT

Novel phenolic cyan dye-forming couplers contain a p-cyanophenylureido group in the 2-position and in the 5-position an acylamino substituent containing a sulfone group having bulky substituents sufficient to provide steric interaction within the coupler molecule and the dye molecule derived therefrom. The couplers are useful in photographic emulsions.

7 Claims, No Drawings

CYAN DYE-FORMING COUPLERS AND PHOTOGRAPHIC MATERIALS CONTAINING SAME

The present invention relates to novel phenolic cyan dye-forming couplers and to photographic elements containing such couplers.

Couplers which are used to obtain cyan dyes for color photography are typically phenols and naphthols. These couplers yield azomethine dyes upon coupling with oxidized aromatic primary amino color developing agents.

U.S. Pat. No. 4,333,999 describes cyan phenolic couplers which comprise a p-cyanophenylureido group in the 2-position of the phenolic ring. This class of couplers has found wide commercial acceptance in photographic applications. Included among the important advantages of these couplers is their ability to yield dyes having improved hue purity, that is, having a narrow absorption band. These dyes also have maximum absorption values beyond about 650 nm. This desirable property provides dyes which absorb relatively smaller amounts of green light.

Couplers of the '999 patent have highly desirable properties in that they can provide dyes of excellent purity and hues which are shifted bathochromically to the long wavelength red absorption region. However, even with these couplers, which have found extensive utility, further improvements in coupler reactivity and enhanced dye absorption continue to be sought. For example, it has been difficult to obtain, with the same coupler, both high coupling effectiveness and a dye of the desired hue purity with long wavelength red absorption. Coupling effectiveness is measured for each coupler of this invention by comparing the gamma or contrast of its dye image sensitometric test curve with that of a control coupler under identical conditions.

The use of sulfone (—SO$_2$—) groups in ballast moieties of cyan coupler compounds has been described in various publications, including Japanese Patent Publication Nos. 105644/1984 (priority of Dec. 10, 1982), 111643/1984 and 111644/1984 (priority of Dec. 17, 1982). However, the coupler structures described therein do not provide the combination of essential moieties which have been found to improve coupling effectiveness while maintaining the desired bathochromic shift and hue purity in subsequently obtained dyes.

Accordingly, couplers are continually being sought which can provide cyan dyes having narrow half-bandwidths (HBW) for improved hue purity, which have long wavelength absorption in the red region of the visible spectrum and which possess desirable coupling effectiveness values.

These objectives are provided in accordance with the present invention which resides in the use of particular sustituent combinations in the 5-position acylamino ballast moiety of cyan phenolic coupler compounds of the general type described in U.S. Pat. No. 4,333,999. These coupler compounds comprise a sulfone (SO$_2$) group and a particular combination of substituent groups adjacent to the sulfone group. The combination includes use of at least one bulky group substituent which is believed to be capable of providing steric interaction with the sulfone moiety and also with other portions of the coupler compound as well as in the resulting image dye. The result is achievement of remarkably higher coupling effectiveness than for couplers of the '999 patent while simultaneously maintaining the desirably pure dye hues in the long wavelength red absorption region.

Coupler compounds which fulfill the requirements noted above, and which fall within this invention, have the following structural formula:

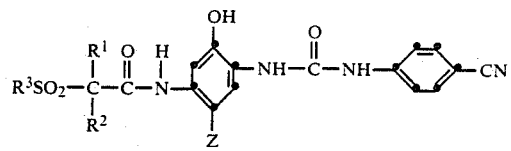

wherein:

R$^1$ is an unsubstituted or substituted, straight or branched chain alkyl group having from 1 to about 20 carbon atoms, an unsubstituted or substituted cycloalkyl group having from 3 to about 8 carbon atoms in the ring, an alkylcarbonyl or an alkoxycarbonyl group having from 1 to about 20 carbon atoms in the alkyl or alkoxy moiety;

R$^2$ is defined for R$^1$ or is hydrogen;

R$^3$ is an unsubstituted or substituted alkyl group having from 1 to about 24 carbon atoms, an unsubstituted or substituted cycloalkyl group having from 3 to about 8 carbon atoms in the ring, an unsubstituted or substituted aryl group having from 6 to about 24 carbon atoms, or an unsubstituted or substituted heterocyclic group having from 3 to about 8 atoms in the heterocyclic ring wherein the hetero ring atoms can be nitrogen, oxygen, or sulfur;

with the proviso that when R$^3$ is a primary alkyl group R$^1$ must contain at least 2 carbon atoms; and Z is hydrogen or a coupling off group.

At least one of the groups R$^1$, R$^2$ and R$^3$ is of such size and configuration as to confer sufficient bulk to provide the desired steric interaction believed responsible for the effects seen in the coupler compounds described herein. In combination, these groups must also provide sufficient ballast to render the coupler compound substantially nondiffusible in a layer of a photographic imaging material in which it is coated.

The specific combination in a phenolic coupler of (1) a para-cyanophenylureido group in the 2-position and (2) a sulfone-containing ballast group in the 5-position, as described for compounds of this invention, provides the desired coupling effectiveness and image dyes with enhanced long wavelength red light absorption. The need for sufficient steric bulk in groups adjacent the SO$_2$ moiety leads to the proviso in the definition of the R$^1$ group as noted above. This is illustrated in examples below. The data show that when R$^3$ is primary alkyl, R$^1$ is methyl, and R$^2$ is hydrogen or methyl, the desired long wavelength dye absorption is not achieved. However, this desired hue is achieved (a) when R$^1$ is methyl and R$^3$ is aryl or secondary alkyl, or (b) when R$^1$ contains 2 or more carbon atoms. The results are surprising and could not have been predicted from the body of knowledge available before the investigations leading to this invention were carried out.

In preferred coupler compounds of this invention R$^1$ is alkyl of 1 to about 20 carbon atoms and R$^2$ is alkyl of 1 to about 4 carbon atoms. In particularly preferred coupler compounds R$^1$ is alkyl of 2 to about 14 carbon atoms and R$^2$ is hydrogen. When the R$^1$ and R$^2$ groups are substituted, such substituents include hydroxy, halogen, or alkoxy having from 1 to about 8 carbon atoms.

When the $R^3$ group is substituted such substituents may include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido and sulfamoyl groups wherein the alkyl and aryl substituents, and the alkyl and aryl moieties of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido and sulfamoyl substituents can contain, respectively, from 1 to about 30 carbon atoms and from 6 to about 30 carbon atoms and can be further substituted with such substituents.

Coupling off groups defined by Z are well known to those skilled in the art. Such groups can determine the equivalency of the coupler i.e., whether it is a 2-equivalent coupler or a 4-equivalent coupler. Such groups can also modify the reactivity of the coupler or can advantageously affect the layer in which the coupler is coated, or other layers in a photographic recording material, by performing, after release from the coupler, such functions as development inhibition, bleach inhibition, bleach acceleration, color correction and the like.

Representative classes of coupling-off groups include alkoxy, aryloxy, heteroyloxy, sulfonyloxy, acyloxy, acyl, heterocyclyl, sulfonamido, phosphonyloxy and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U.K. Patents and published applications Nos. 1,466,728, 1,531,927, 1,533,039, 2,006,755A and 2,017,704A, the disclosures of which are incorporated herein by reference.

Examples of preferred coupling-off groups which can be represented by Z are:

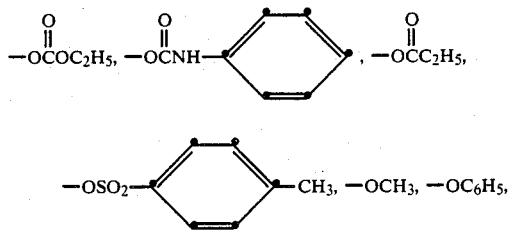

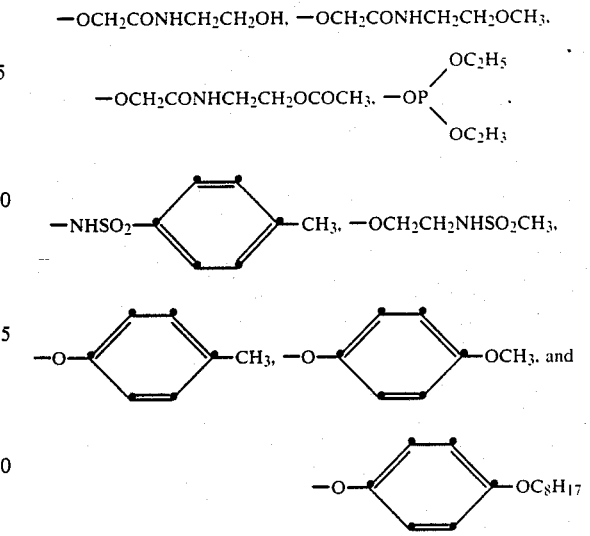

Especially preferred Z groups are hydrogen and

where $R^6$ is an alkyl or an alkoxy group having from 1 to about 10 carbon atoms.

The desirable objectives of this invention are attained by particular combinations of substituent groups on the ballast moiety of the coupler compounds. For example, bulky substituent groups, when present in at least one of the positions represented by $R^1$, $R^2$ and $R^3$, which substituents are spatially arranged so that steric interaction between them and the $SO_2$ moiety, or with adjacent position substituents on the coupler molecule, result in cyan dyes having desirably narrow bandwidths while absorbing red light at relatively longer wavelengths.

Specific coupler compounds of this invention are shown below in Table 1 with reference to the following structural formula:

TABLE 1

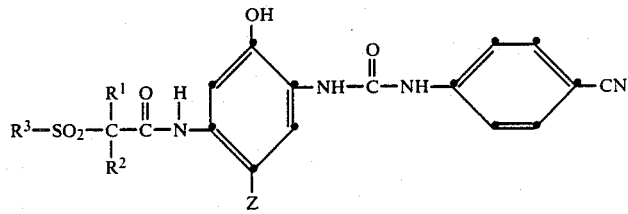

| Coupler Compound | $R^1$ | $R^2$ | $R^3$ | Z* |
|---|---|---|---|---|
| 1 | $-C_2H_5$ | H | $-C_{16}H_{33}$ | A |
| 2 | $-C_3H_7-i$ | " | $-C_{16}H_{33}$ | " |
| 3 | $-C_{14}H_{29}$ | " | $-CH_3$ | " |
| 4 | $-C_4H_9$ | " | $-CH_{18}H_{37}$ | " |
| 5 | $-C_{10}H_{21}$ | " | $-C_{18}H_{37}$ | " |
| 6 | $-C_2H_5$ | " | $-C_{16}H_{33}$ | H |
| 7 | $-C_2H_5$ | " | $-C_{16}H_{33}$ | B |

TABLE 1-continued

General structure:

$$R^3-SO_2-\underset{R^2}{\underset{|}{\overset{R^1}{\overset{|}{C}}}}-\overset{O}{\overset{\|}{C}}-\overset{H}{\overset{|}{N}}-\text{[2-OH, 5-Z phenyl]}-NH-\overset{O}{\overset{\|}{C}}-NH-\text{[phenyl]}-CN$$

| Coupler Compound | R¹ | R² | R³ | Z* |
|---|---|---|---|---|
| 8 | —CH₃ | " | —CH(C₁₀H₂₁)COOCH₃ | A |
| 9 | —CH₃ | —CH₃ | 4-(NHSO₂C₁₆H₃₃)phenyl | B |
| 10 | —C₂H₅ | H | " | A |
| 11 | —C₂H₅ | " | 3-(NHSO₂C₁₆H₃₃)phenyl | " |
| 12 | —C₁₀H₂₁ | " | 3-[NHSO₂-(2-COOH-phenyl)]phenyl | " |
| 13 | —C₁₀H₂₁ | " | 3-[NHSO₂-(4-OH-phenyl)]phenyl | " |
| 14 | —C₂H₅ | " | 4-(OSO₂C₁₆H₃₃)phenyl | A |
| 15 | —C₂H₅ | " | 3-OCH₃-4-(OSO₂C₁₆H₃₃)phenyl | " |
| 16 | —C₂H₅ | " | 4-(C₁₅H₃₁)phenyl | " |
| 17 | —C₂H₅ | H | 4-(OC₁₂H₂₅)phenyl | " |

TABLE 1-continued

Structure:

R³—SO₂—C(R¹)(R²)—C(=O)—NH—[phenyl with OH and Z]—NH—C(=O)—NH—[phenyl]—CN

| Coupler Compound | R¹ | R² | R³ | Z* |
|---|---|---|---|---|
| 18 | —C₂H₅ | " | [methyl-phenyl]—COOC₁₆H₃₃ | " |
| 19 | —C₁₀H₂₁ | " | [methyl-phenyl]—OH | " |
| 20 | —COCH₂CH₂CH₃ | " | [1-methyl-4-phenyl-tetrazolyl: N=N / N—N—C₆H₅] | " |
| 21 | —COC₉H₁₉ | " | [methyl-thiophenyl, S] | " |
| 22 | [cyclohexyl] | " | —C₁₆H₃₃ | " |
| 23 | —CH₃ | " | —CH(C₁₆H₃₃)CH₃ | B |

*A = —O—[phenyl]—OCH₃

B = —O—[phenyl]—OC₈H₁₇

Couplers of this invention can be prepared by reacting p-cyanophenylisocyanate with an appropriate aminophenol, such as 2-amino-5-nitrophenol or 2-amino-4-chloro-5-nitrophenol to form the 2-(p-cyanophenyl)ureido compound. The nitro group can then be reduced to an amine, and the ballast group attached thereto by conventional procedures. Two equivalent couplers can be prepared by known techniques, for example, by substitution of the 4-chloro group on the starting phenol or by a synthetic route shown below in the preparation of Coupler Compound No. 1 of this invention.

Synthesis I

Preparation of Coupler Compound No. 1 was accomplished according to the following synthetic scheme:

A. Preparation of phenolic coupler moiety (S-4)

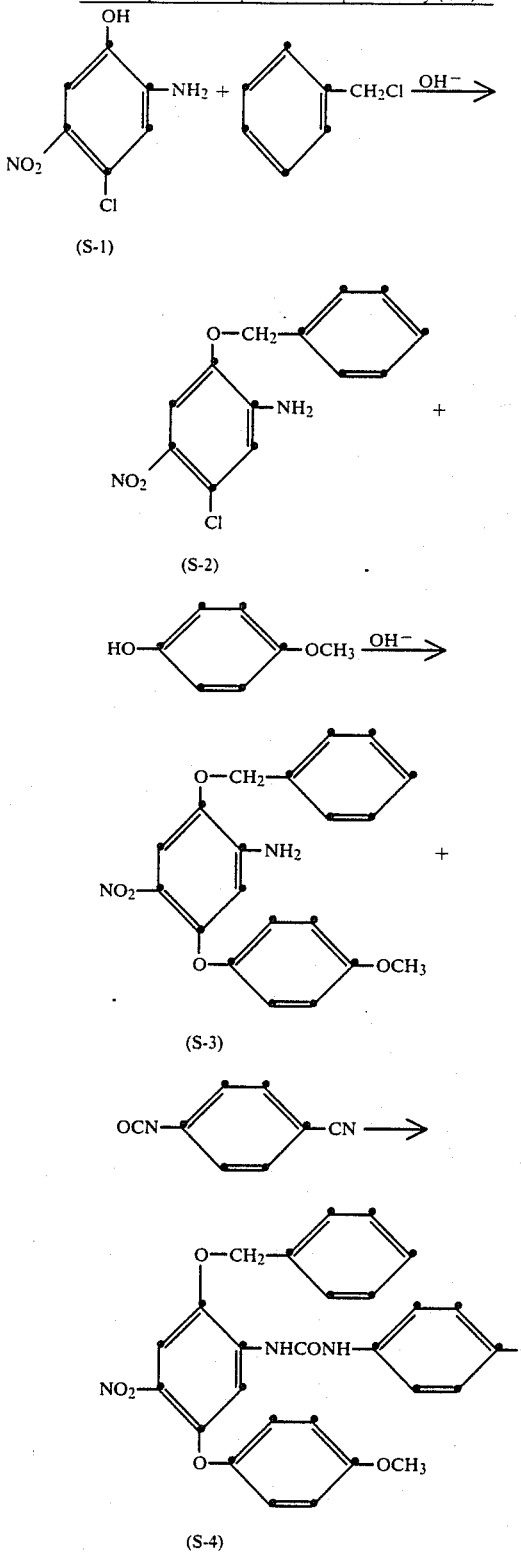

Preparation of the blocked 2-p-cyanophenylureido-4-p-methoxy-phenoxy-5-nitrophenol moiety (S-4)

To a refluxing solution of 33.7 g (0.2 mol) 2-amino-4-chloro-5-nitrophenol (S-1) and 12.8 g (0.2 mol) potassium hydroxide in 300 ml acetone was added over a 3 hour period 25.3 g (0.2 mol) α-chlorotoluene. After an additional 6 hour reflux, the mixture was concentrated and added to excess cold potassium carbonate solution. The resulting precipitate was washed, dried, and recrystallized from xylene to yield 44.8 g yellow-green solid S-2, m.p. 131°.

A solution of 9.4 g (0.076 mol) p-methoxyphenol and 4.3 g (0.076 mol) potassium hydroxide in 200 ml toluene was refluxed to remove the aqueous azeotrope, then cooled to 40°. Then 40 ml dimethyl sulfoxide and 12 g (0.043 mol) S-2 were added sequentially and the mixture was heated gradually and refluxed 1 hour. The cooled reaction mixture was washed with water and sodium carbonate solution, dried over magnesium sulfate and treated with carbon. The solid obtained by cooling the concentrated, and filtering was washed with toluene and hexane then dried to yield 11.5 g S-3.

This product was coverted to S-4 by treatment with equimolar p-cyanophenylisocyanate according to a procedure analogous to that described in Example 1 of U.S. Pat. No. 4,333,999, the disclosure of which is hereby incorporated by reference.

B. Preparation of ballast moiety

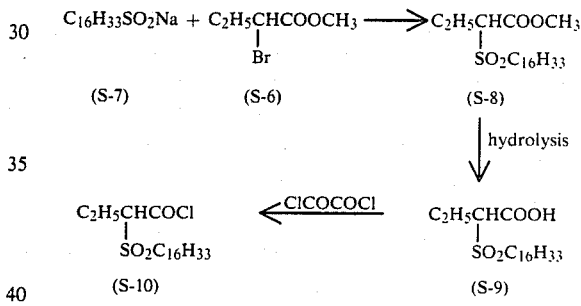

Preparation of ballasted acid chloride S-10

To a well-stirred solution of 25.2 g (0.2 mol) sodium sulfate and 16.8 g (0.2 mol) sodium carbonate in 200 ml water was added a solution of 33 g (0.1 mol) hexadecanesulfonyl chloride in 150 ml 1:1:1 tetrahydrofuran/acetonitrile/acetone. After 4 hours the mixture was concentrated and the white solid product taken up in hot methanol to remove insoluble salts. Concentration of filtrate yielded 25 g white crystalline S-7.

A suspension of 20 g (0.063 mol) S-7 and 29 g (0.158 mol) methyl α-bromobutyrate (S-6) was stirred at reflux 26 hours then cooled to room temperature. The resulting solid was extracted with hot methylene chloride. The filtrates were concentrated and purified by silica gel chromatography to obtain 3.3 g of white solid S-8 ester with the expected mass spectrum. This ester was dissolved in 30 ml tetrahydrofuran and 20 ml methanol and treated with 2 g sodium hydroxide in 15 ml water for 0.5 hour. Treatment with hydrochloric acid and washing yielded 3 g white solid S-9 acid which was further treated with 1.95 g (0.015 mol) oxalyl chloride in 100 ml methylene chloride to give the yellow solid S-10 ballasted acid chloride.

Alternate preparation of ballast moiety

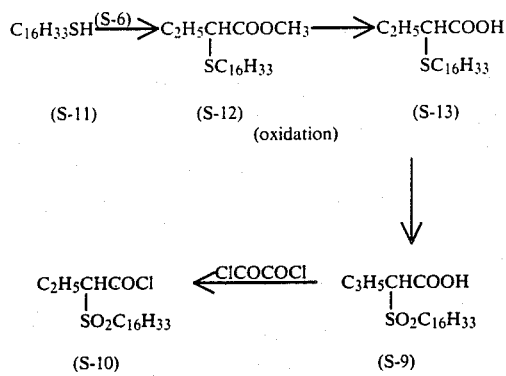

Alternative 2 for preparation of ballasted acid chloride S-10

To a well-stirred solution of 258.4 g (1 mol) n-hexadecyl mercaptan (S-11) and 217 g (1.2 mol) methyl alpha-bromobutyrate (S-6) in 500 ml ethanol was added, under nitrogen, a solution of 44 g (1.1 mol) sodium hydroxide in 300 ml water. After 1 hour a solution of 80 g (2 mol) sodium hydroxide in 1 liter tetrahydrofuran and 750 ml methanol was added and stirring continued 2 hours to hydrolyze the S-12 ester to the S-13 acid sodium salt. This salt, which precipitated on concentration of the reaction mixture, was suspended in 4.5 liters dilute hydrochloric acid and stirred 1 hour to yield 350 g moist white solid S-13 acid.

A solution of 1 g tungstic acid in aqueous sodium hydroxide was made slightly acidic by titration with acetic acid and then added at 30° to a solution of 290 g S-13 acid in 1.15 liters acetic acid. To this solution was added dropwise with stirring over a 30 minute period 210 g (1.85 mol) of 30% hydrogen peroxide solution. After 2 hours additional stirring, a white crystalline product was isolated by filtration. Washing with ligroin and acetonitrile yielded 233 g S-9 acid. This was converted to the S-10 ballasted acid chloride by treatment with equimolar oxalyl chloride, as described above.

C. Coupler formation

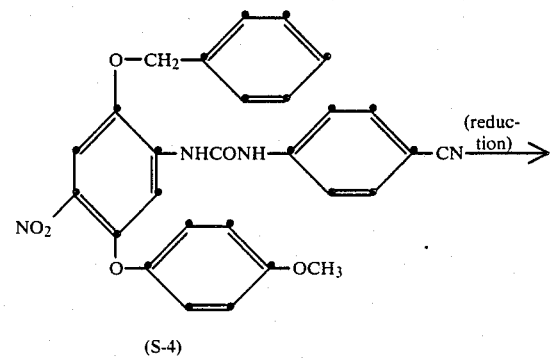

-continued
C. Coupler formation

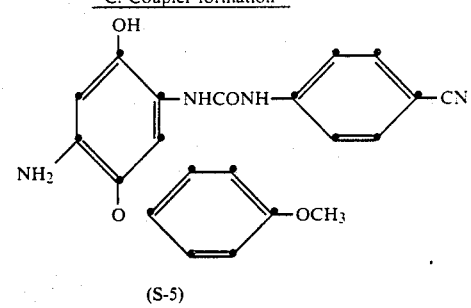

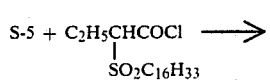

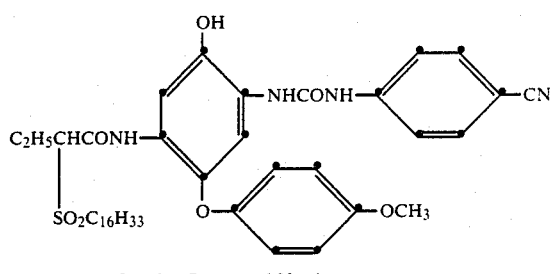

Coupler Compound No. 1

A suspension of 3.9 g (0.008 mol) nitro compound S-4 (Preparation A above) in Ethyl Acetate was shaken overnight under 40 psi hydrogen in the presence of 1.5 g 10% palladium on carbon catalyst and 0.5 ml acetic acid to yield the amino compound S-5. Then 0.008 mol of ballasted acid chloride S-10 and 2.8 g (0.023 mol) dimethylaniline were added under nitrogen and the mixture stirred for 15 minutes. Removal of catalyst by filtration, dilute hydrochloric acid washing, concentration to solid and crystallization from acetonitrile yielded 3.3 g of light tan solid Coupler Compound No. 1 with the correct element analysis and mass spectrum.

Synthesis 2

Preparation of Coupler Compound No. 14 was accomplished according to the following synthetic scheme:

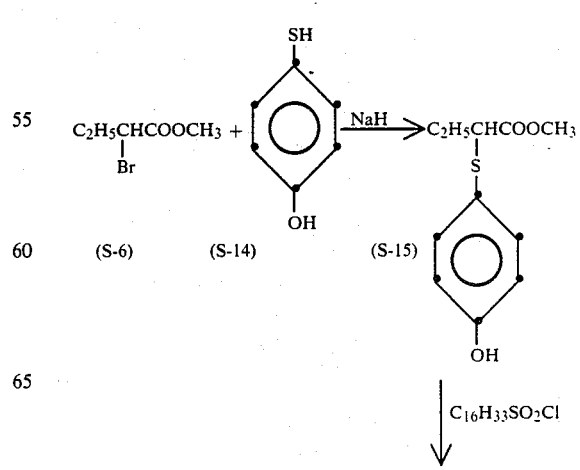

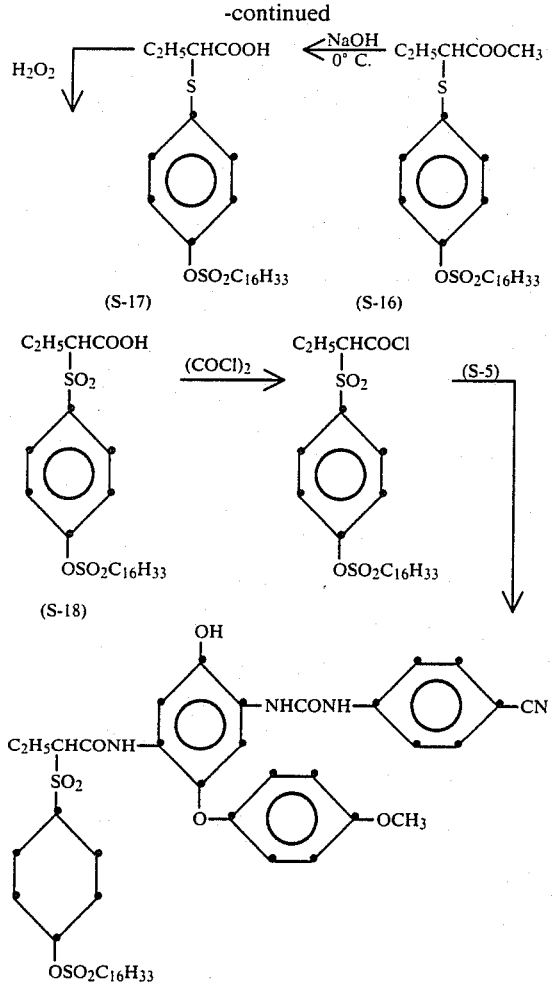

Coupler Compound No. 14

The cyan dye-forming couplers of this invention can be used in the ways and for the purposes that cyan dye-forming couplers are used in the photographic art. Typically, the couplers are incorporatd in silver halide emulsions and the emulsions coated on a support to form a photographic element. Alternatively, the couplers can be incorporated in photographic elements adjacent the silver halide emulsion where, during development, the coupler will be in reactive association with development products such as oxidized color developing agent.

As used herein, the term "associated therewith" signifies that the coupler is in the silver halide emulsion layer or in an adjacent location where, during processing, it is capable of reacting with silver halide development products.

The photographic elements can be either single color or multicolor elements. In a multicolor element, the cyan dye-forming coupler of this invention is usually associated with a red-sensitive emulsion, although it could be associated with an unsensitized emulsion or an emulsion sensitized to a different region of the spectrum. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprised of at least one red-sensitive silver halide emulsion layer having associated therewith at least one cyan dye-forming coupler, at least one of the cyan dye-forming couplers being a coupler of this invention, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the elements of this invention, reference will be made to Research Disclosure, December 1978, Item 17643, published by Industrial Opportunities Ltd., Homewell Havant, Hampshire, P09 1EF, U.K., the disclosures of which are incorporated herein by reference. This publication will be identified hereafter by the term "Research Disclosure."

The silver halide emulsions employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers described herein the elements of this invention can include additional couplers as described in Research Disclosure Section VII, paragraphs D, E, F and G and the publications cited therein. These additional couplers can be incorporated as described in Research Disclosures of Section VII, paragraph C and the publications cited therein.

The photographic elements of this invention can contain brighteners (Research Disclosure Section V), antifoggants and stabilizers (Research Disclosure Section VI), antistain agents and image dye stabilizers (Research Disclosure Section VII, paragraphs I and J), light absorbing and scattering materials (Research Disclosure Section VIII), hardeners (Research Disclosure Section XI), plasticizers and lubricants (Research Disclosure Section XII), antistatic agents (Research Disclosure Section XIII), matting agents (Research Disclosure Section XIII), matting agents (Research Disclosure Section XVI), and development modifiers (Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-β-(methanesulfonamido)ethylaniline sulfate hydrate, 4-amino-3-methyl-N-ethyl-N-β-hydroxyethylaniline sulfate, 4-amino-3-β-(methanesulfonamido)ethyl-N,N-diethylaniline hydrochloride and 4-amino-N-ethyl-N-diethylaniline hydrochloride and 4-amino-N-ethyl-N-(2-methoxyethyl)-m-toluidine di-p-toluene sulfonic acid.

With negative working silver halide this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

In the following examples, a measure of each coupler's coupling effectiveness is represented by G, the ratio of its photographic dye image gamma (the slope of the sensitometric curve) to that of Control Coupler A, which is normalized to 1.0. Coupler A is identical to Coupler No. 7 of U.S. Pat. No. 4,333,999. Such normalization of the data compensates for coating and processing variations by relating the performance of each test coupler to that of a control coupler coated and processed at the same time. In these comparisons 2-equivalent couplers were coated at one-half the silver level of 4-equivalent couplers.

Normalization of the data compensates for coating and processing variations by relating the performance of each coupler as described herein to that of a control coupler coated and processed at the same time and in the same manner. In these comparisons 2-equivalent couplers were coated at one-half the silver level of 4-equivalent couplers.

Processing and testing procedures were kept constant. Hue measurements on a normalized spectral absorption curve included λmax (the peak absorption wavelength) and HBW (the half bandwidth). The HBW value serves to indicate hue purity. Dye images of narrow HBW and of λmax>680 are least likely to have unwanted absorption tailing into the green region. Particularly useful couplers provided dye images with G>1.00, λmax>680 nm and HBW<150 nm.

The following examples further illustrate this invention.

EXAMPLE 1

Photographic elements were prepared by coating a cellulose acetate film support with a light-sensitive layer comprising a silver bromoiodide emulsion at 0.46 g Ag/m², gelatin at 3.78 g/m² containing a cyan phenolic coupler identified by number as shown above in Table I. Each coupler was dispersed in one half its weight of di-n-butylphthalate and coated at $1.62 \times 10^{-3}$ moles/m². The photosensitive layer was overcoated with a layer containing gelatin at 1.08 g/m² and the hardener compound bis-vinylsulfonylmethyl ether at 1.75 weight percent based on total gelatin.

Samples of each element were imagewise exposed through a graduated-density test object and processed at 40° C. employing the following color developing solution, then stopped, bleached with a ferric EDTA solution, fixed, and washed to produce stepped cyan dye images.

| | |
|---|---|
| $K_2SO_3$ | 2.0 g |
| $K_2CO_3$ (anhydrous) | 30.0 g |
| KBr | 1.25 g |
| KI | 0.6 g |
| 4-Amino-3-methyl-N—ethyl N—β-hydroxyethylaniline sulfate | 3.55 g |
| Water to 1.0 liter | pH 10.0 |

Results are noted below in Table II:

TABLE II

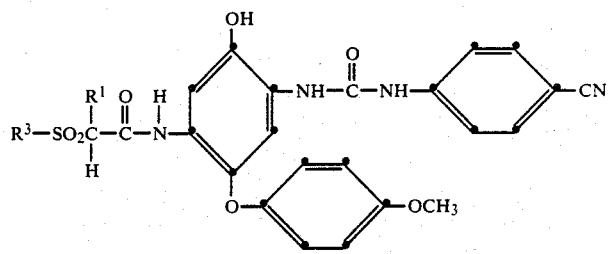

| Coupler Compound No. | $R^1$ | $R^3$ | G | λmax, nm | HBW, nm |
|---|---|---|---|---|---|
| Control A | | (See structure) | 1.00 | 690 | 140 |
| Control B | —CH₃ | —C₁₆H₃₃ | 1.19 | 615 | 145 |
| 1 | —C₂H₅ | —C₁₆H₃₃ | 1.78 | 694 | 118 |
| 2 | —C₃H₇—i | —C₁₆H₃₃ | 1.45 | 697 | 130 |
| 3 | C₁₄H₂₉ | —CH₃ | 1.49 | 691 | 128 |
| 4 | C₄H₉ | —C₁₈H₃₇ | 1.68 | 684 | 122 |
| 6* | —C₂H₅ | —C₁₆H₃₃ | 2.12 | 690 | 128 |

TABLE II-continued
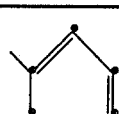
| Coupler Compound No. | $R^1$ | $R^3$ | G | λmax, nm | HBW, nm |
|---|---|---|---|---|---|
| 11 | $-C_2H_5$ | 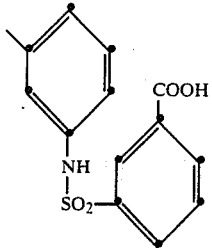 | 2.30 | 695 | 122 |
| 12 | $-C_{10}H_{21}$ | 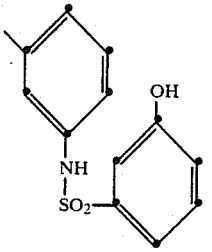 | 1.85 | 690 | 128 |
| 13 | $-C_{10}H_{21}$ | 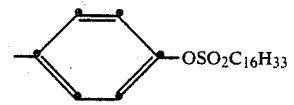 | 1.25 | 692 | 134 |
| 14 | $-C_2H_5$ | 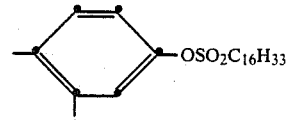 | 1.70 | 687 | 108 |
| 15 | $-C_2H_5$ | 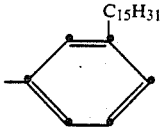 | 1.35 | 681 | 133 |
| 16 | $-C_2H_5$ | 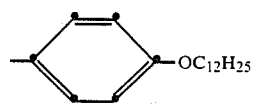 | 1.16 | 695 | 96 |
| 17 | $-C_2H_5$ | | 1.84 | 683 | 117 |

TABLE II-continued

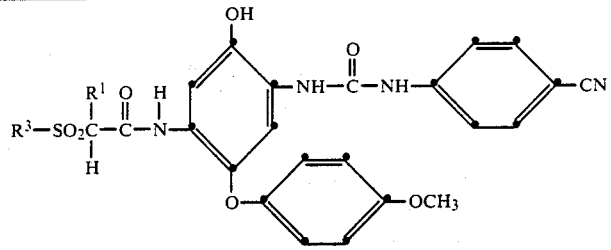

| Coupler Compound No. | $R^1$ | $R^3$ | G | λmax, nm | HBW, nm |
|---|---|---|---|---|---|
| 18 | $-C_2H_5$ | $COOC_{16}H_{33}$ (phenyl) | 1.09 | 696 | 111 |
| 19 | $-C_{10}H_{21}$ | OH (phenyl) | 1.33 | 714 | 130 |

*Coupling-off group is H
Coupler A: (Coupler No. 7 in U.S. Pat. No. 4,333,999)

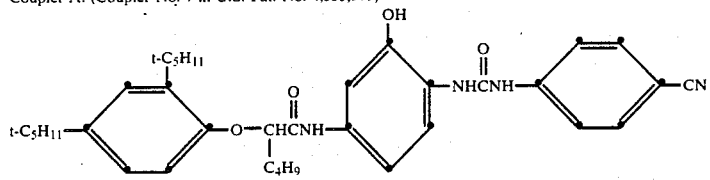

From the above comparisons it can be ssen that appreciable improvements in absorption values towards longer wavelengths (λmax) as well as in dye purity (narrow HBW), result from dyes derived from the couplers of this invention. The significant increase in coupling effectiveness (G), obtainable by this invention is seen by comparison with the prior art represented by Control Coupler A. Especially noteworthy is the marked bathochromic hue shift and absorption band narrowing achieved by changing $R^1$ from methyl (Control Coupler B) to ethyl or isopropyl (inventive Couplers Nos. 1 and 2). This confirms the belief that at least one bulky group adjacent to the $R^5SO_2$ group is needed for steric interactions to provide the desired effects. That $R^5$ itself need not be bulky is shown by comparing data for Coupler No. 3 with that for Control Coupler B.

EXAMPLE 2

Photographic elements were prepared, exposed, and processed as described in Example 1 using the couplers shown in Table III with the following results:

TABLE III

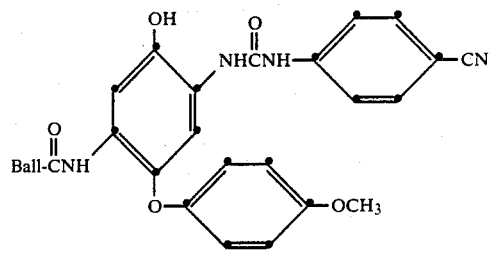

| Coupler No. | Ball- | G | λmax nm | HBW nm |
|---|---|---|---|---|
| B | $-C_{16}H_{33}SO_2CH-$ with $CH_3$ | 1.19 | 615 | 145 |
| C | $-C_{16}H_{33}SO_2C-$ with two $CH_3$ | 1.81 | 676 | 159 |

TABLE III-continued

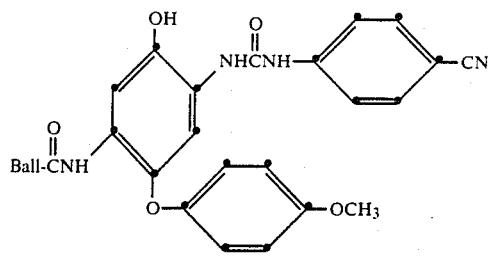

| Coupler No. | Ball- | G | λmax nm | HBW nm |
|---|---|---|---|---|
| 8 | $\underset{\underset{CH_3}{|}}{C_{10}H_{21}CHSO_2CH-}\overset{COOCH_3}{|}$ | 1.41 | 690 | 149 |
| D | $-CH_{16}H_{33}SCH-\overset{C_2H_5}{|}$ | 1.73 | 664 | 175 |
| 9 | $C_{16}H_{33}SO_2NH-\langle\text{ring}\rangle-SO_2\underset{\underset{CH_3}{|}}{\overset{CH_3}{|}}C-$ | 1.37 | 690 | 169 |
| 10 | $C_{16}H_{33}SO_2NH-\langle\text{ring}\rangle-SO_2CH-\overset{C_2H_5}{|}$ | 2.05 | 683 | 123 |

The data of Table III illustrate the need for sufficient steric bulk in the ballast groups adjacent to the SO$_2$ moiety. Comparison coupler Compounds B and C wherein R$^1$ is methyl and R$^3$ is a primary alkyl group do not yield dyes of sufficiently bathochromic hue. However, converting R$^3$ into a secondary alkyl group, as in coupler Compound 8 of the invention, is sufficient to render the dye absorption more bathochromic. This effect is believed to be dependent on the steric crowding of the SO$_2$ group by the flanking methyl and carbomethoxy groups. The rather minor structural change from a methyl (R$^1$) group of coupler Compound B to ethyl, as in coupler Compound 1 of the invention, provides a dye showing a remarkable bathochromic shift and band narrowing as well as an improvement in coupling effectiveness. When the SO$_2$ moiety of coupler Compound 1 is changed to the less bulky S moiety, as in comparison coupler Compound D, the steric interaction is lost and a hypsochromically shifted dye results. The data for coupler Compounds 9 and 10 show that dyes with absorption maxima beyond 680 nm can result when the ballast moiety contains an R$^3$ aryl group in combination with either a methyl or ethyl R$^1$ group.

This invention has been described in detail with particular reference to preferred embodiments thereof, but it will be understood that variations and modifications can be effected within the spirit and scope of the invention.

What is claimed is:

1. A photographic element comprising a support and a photosensitive silver halide emulsion which has associated therewith a cyan dye-forming coupler compound having the structural formula:

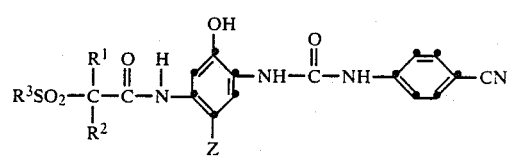

wherein:
R$^1$ is an unsubstituted or substituted, straight or branched chain alkyl group having from 1 to about 20 carbon atoms, an unsubstituted or substituted cycloalkyl group having from 3 to about 8 carbon atoms in the ring, an alkylcarbonyl or an alkoxycarbonyl group having from 1 to about 20 carbon atoms in the alkyl or alkoxy moiety;

R$^2$ is defined for R$^1$ or is hydrogen;

R$^3$ is an unsubstituted or substituted alkyl group having from 1 to about 24 carbon atoms, an unsubstituted or substituted cycloalkyl group having from 3 to about 8 carbon atoms in the ring, an unsubstituted or subsituted aryl group having from 6 to about 24 carbon atoms, or an unsubstituted or substituted heterocyclic group having from 3 to about 8 atoms in the heterocyclic ring wherein the hetero ring atoms can be nitrogen, oxygen, or sulfur;

with the proviso that when R$^3$ is a primary alkyl group R$^1$ must contain at least 2 carbon atoms; and Z is hydrogen or a coupling off group.

2. The photographic element of claim 1 wherein R$^1$ is alkyl of from 1 to about 20 carbon atoms and R$^2$ is alkyl of from 1 to about 4 carbon atoms.

3. The photographic element of claim 1 wherein R$^4$ is alkyl of from 2 to about 14 carbon atoms and R$^2$ is hydrogen.

4. The photographic element of claim 1 wherein at least one of $R^1$ and $R^2$ is substituted with hydroxy, a halogen atom or an alkoxy group having from 1 to about 8 carbon atoms.

5. The photographic element of claim 1 wherein Z is hydrogen or

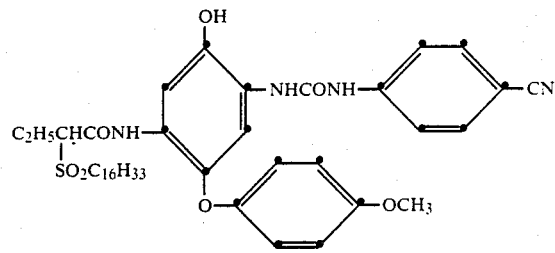

where $R^6$ is an alkyl or an alkoxy group having from 1 to about 10 carbon atoms.

6. The photographic element of claim 1 wherein the cyan dye-forming coupler compound has the structural formula:

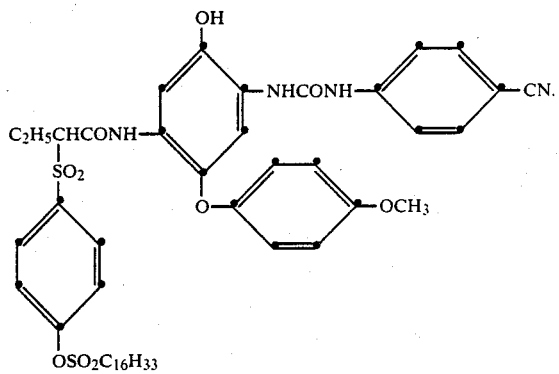

7. The photographic element of claim 1 wherein the cyan dye-forming coupler compound has the structural formula:

* * * * *